United States Patent [19]

Yates et al.

[11] Patent Number: 4,922,044

[45] Date of Patent: May 1, 1990

[54] PURIFICATION OF CHLOROFORM

[75] Inventors: Stephen F. Yates, Arlington Heights; Hermann A. Zinnen, Evanston, both of Ill.

[73] Assignee: Allied-Signal Inc., Morris Township, Morris County

[21] Appl. No.: 267,058

[22] Filed: Nov. 4, 1988

[51] Int. Cl.$^5$ ............................................. C07L 17/38
[52] U.S. Cl. ..................................... 570/263; 570/262
[58] Field of Search .............................. 570/262, 263

[56] References Cited

U.S. PATENT DOCUMENTS

| 1,825,814 | 10/1931 | Norris | 570/262 |
| 2,024,095 | 12/1935 | Daudt et al. | 260/653.7 |
| 2,178,695 | 4/1938 | Muskat et al. | 260/652 |
| 2,829,180 | 4/1958 | Montgomery et al. | 260/662 |
| 3,215,747 | 11/1965 | Fainberg et al. | 260/653.3 |
| 3,218,364 | 11/1965 | Kometani et al. | 260/653.3 |
| 3,804,910 | 4/1974 | Furrow | 260/653.3 |

FOREIGN PATENT DOCUMENTS

| 47-37402 | 9/1972 | Japan . |
| 48-23059 | 7/1973 | Japan . |
| 52-62207 | 5/1977 | Japan . |
| 55500 | 5/1968 | Poland . |
| 1312265 | 4/1973 | United Kingdom . |
| 1406502 | 9/1975 | United Kingdom . |
| 1438246 | 6/1976 | United Kingdom . |

OTHER PUBLICATIONS

Allied Chemical Corporation Proposal, Letters from Union Carbide and Vulcan Materials Company, 1971.

*Primary Examiner*—Howard T. Mars
*Attorney, Agent, or Firm*—Jay P. Friedenson; Harold N. Wells

[57] ABSTRACT

Industrial grade chloroform is purified to remove traces of cis-1,2-dichloroethylene, bromochloromethane, and amylenes by a two-step process. The chloroform is first treated by contacting with aqueous sulfuric acid to remove amylenes and thereafter passed over a zeolite having an average pore size of 3 to 6 Angstroms and a Si/Al atomic ratio in the range of about 1.6/1 to 3/1, preferably calcium chabazite, to remove cis-1,2-dichloroethylene and bromochloromethane.

9 Claims, No Drawings

PURIFICATION OF CHLOROFORM

The invention relates generally to improvement of the process for making difluorochloromethane, CHClF2, designated also as refrigerant 22 (R22). More particularly, the invention relates to purification of the feedstock for such a process, namely chloroform.

It has been found that when chloroform is reacted with hydrogen fluoride in the presence of antimony pentachloride catalyst, minor impurities in the chloroform build up in the reactor since the R22 product is vaporized as produced. Periodically, it becomes necessary to cease operations, empty the reactor, and dispose of the catalyst along with the accumulated impurities introduced with the chloroform and any high-boiling heavy compounds produced during the reaction. Such a process is illustrated generally in U.S. Pat. No. 2,024,095, however, there is no indication of the problem just discussed. Removal of such minor impurities can extend the period in which a reactor may be operated efficiently without requiring a shutdown.

Chloroform is principally produced by direct chlorination of methane, which yields dichloromethane, chloroform (trichloromethane), and tetrachloromethane. U.S. Pat. No. 2,829,180 is illustrative. The chloroform is typically quite pure but includes ppm quantities (e.g. 50–500 ppm) of various byproducts, including cis-1,2-dichloroethylene, 1,1-dichloroethane, amylenes, bromochloromethane, and carbon tetrachloride.

Bromochloromethane is undesirable since it is converted to chlorofluoromethane, which is toxic and therefore should not be present in R22.

Amylenes may be added by the chloroform producer as an inhibitor. Such heavier materials are not distilled over with the CHClF2 product and therefore accumulate in the reactor. They may also react to form even higher boiling compounds.

Cis-1,2-dichloroethylene also reacts to form heavy byproducts which accumulate and require reactor shutdowns as described above.

Many patents have disclosed methods of preparing and purifying chloroform, but generally they have not been concerned with the very small amounts of impurities (i.e. up to about 1000 wt ppm) of concern to the present inventors. One exception is Japanese published application 62207/77 in which the applicants disclose their use of a synthetic A-type zeolite having an effective pore diameter of about 3.0–5.5 Å to remove impurities (cis 1,2-dichloroethylene, chlorobromomethane or dichloromethane).

The patentees report that 1,2-dichloroethylene, chlorobromomethane, and dichloromethane are almost completely removed. They indicate that the zeolites can be regenerated by passing air at 300° C. over it for 16 hours. Some loss of adsorptive capacity was shown. Amylenes were not mentioned nor was there any suggestion of the usefulness of other adsorbents.

Removal of brominated hydrocarbons from chloroform is discussed in GB 1,438,246. Chloroform is passed in the vapor phase over active carbon, aluminum oxide, or chromium oxide as a catalyst which causes a reaction between chloroform and chlorobromomethane to produce a higher boiling compound separable by distillation. In GB 1,406,502 removal of bromine from chlorinated hydrocarbons is accomplished by contacting with an aqueous solution of sulfur dioxide, a sulfite or a bisulfite. The removal of bromochloromethane from chloroform is accomplished by contacting it with a solid Friedel-Crafts catalyst such as AlCl3 according to GB 1,312,265.

A number of patents and applications have been concerned with purification of chloroform, although not necessarily in connection with the production of CHClF2. Two Japanese published applications, J72/37402 and J73/23059, describe purification of chloroform in a sequence of treatments, namely Amberlyst A21 followed by 4A molecular sieves and then sodium carbonate or activated carbon followed by Amberlyst A21 and then 3A molecular sieves.

Treatment of halogenated hydrocarbons by sulfuric acid has been suggested in many patents. For example, in U.S. Pat. No. 2,178,695 "unstable compounds" are removed from halogenated hydrocarbons by treatment with sulfuric acid. The patentees state that their material was substantially free of unsaturated compounds and thus, the "unstable compounds" may be presumed not to be unsaturated. Purification of crude chloroform by sulfuric acid has been mentioned in Polish patent 55,500 as part of a sequence of extraction and distillation steps.

A combination process for purifying tetrafluoroethylene prior to polymerization is described in U.S. Pat. No. 3,804,910. The feedstock is first treated with sulfuric acid to remove olefinic impurities e.g. trifluoroethylene, difluoroethylene, and terpene hydrocarbons, followed by contact with a 5–10 Å molecular sieve to remove trifluoroethylene. Finally, the tetrafluoroethylene is passed over pyrophoric copper. The patents referenced in the '910 patent, namely U.S. Pat. Nos. 3,215,747 and 3,218,364, provide additional information. It is of interest that in the '747 patent synthetic zeolites are preferred while natural zeolites such as chabazite are mentioned as having pore diameters which are generally too small for purifying tetrafluoroethylene and as being unavailable in sufficient quantities for commercial use. It is also stated that there is no critical upper limit on the pore size and 10 Å and 13 Å are suggested.

The art discussed above relates to particular problems faced by the patentees. They have not (except for Japanese published application 62207/77) been concerned with the present inventors' problem, namely, the interference of trace impurities with the efficient production of refrigerant 22, CHClF2. The inventors have found that a sequence of purification steps will make possible nearly complete removal of the troublesome impurities.

SUMMARY OF THE INVENTION

Chloroform containing only traces of impurities, i.e. up to about 1000 wt. ppm each of cis-1,2-dichloroethylene, bromochloromethane, and amylenes is purified to remove substantially all of said impurities, in order to improve the efficiency of producing refrigerant 22, i.e. CHClF2. The chloroform is first treated with one volume of 80 to 100 wt. % aqueous sulfuric acid, preferably above 90 wt.%, for each 50 to 800 volumes of chloroform at a temperature of about 10° to 150° C. to remove the amylenes. Thereafter, the partially purified chloroform is passed over a sufficient amount of a zeolite having an average pore diameter of 3 to 6 Angstroms and a Si/Al atomic ratio of about 1.6/1 to 3/1 at a temperature of about 10° to 150° C., preferably about 20° to 80° C., and a liquid hourly space velocity up to about 9 hr.$^{-1}$ to remove substantially all of the cis-1,2-dichloroethylene and bromochloromethane. Preferably, the zeolite is dehydrated chabazite, containing calcium ions at the exchangeable sites.

In another aspect of the invention all of the stated impurities are adsorbed by passing the chloroform over a sufficient amount of the zeolite as defined above, preferably chabazite.

DESCRIPTION OF THE PREFERRED EMBODIMENTS

Removing Amylenes

As previously explained, amylenes (unsaturated $C_5$ hydrocarbons) are added to chloroform to remove any residual HCl which can corrode equipment in which it is stored and shipped. Although the amounts used are small, say about 15 to 60 wt. ppm, they can contribute to the problem discussed above.

It has been found that by proper selection of adsorbents that amylenes as well as halogenated hydrocarbon impurities can be substantially reduced. Complete removal of amylenes can be achieved by contact of the chloroform with aqueous sulfuric acid and this method is preferred. If any amylenes should fall to be removed or if it is necessary to bypass acid scrubbing, the downstream solid adsorbent should be selected to remove amylenes also. Generally, contacting chloroform with aqueous sulfuric acid would be expected to remove all of the amylenes, as will be seen in the subsequent examples. It is of particular interest that under preferred contacting conditions, aqueous sulfuric acid appears to leave the cis-1,2-dichloroethylene in the chloroform despite the fact that it is olefinic. Thus, the scrubbing with acid is considered specific to removal of amylenes.

The aqueous sulfuric acid may be of various concentrations, generally from 80 to 100 wt.% but 90 to 96 wt.% is preferred. Since the amount of amylenes present is quite small the volume of acid will be usually much greater than needed to react with the amylenes, consequently, a given quantity of acid may be used to treat a substantial volume of chloroform. The volume ratio of acid to chloroform could be from about 1:50 to 1:800 to remove the composites in a batch process. However, in commercial practice more nearly equal volumes would be used to assure good contacting of the acid with the chloroform. The reaction products, such as alkyl sulfates, may be separated from the acid by distillation.

Typically, the chloroform to be treated will be brought into contact with aqueous sulfuric acid for a suitable period of time, say from 5 seconds to 10 minutes and then phase-separated. Those skilled in the art will appreciate that such contacting and separation may be done in many ways while remaining within the scope of the invention.

The operating pressure preferably will be one which maintains chloroform in the liquid phase at an operating temperature of about 10° to 150° C.

Removing cis-1,2-dichloroethylene

Cis-1,2-dichloroethylene forms heavy products during the fluorination of chloroform and should be removed. While amylenes can be removed by aqueous sulfuric acid scrubbing as discussed above, cis-1,2-dichloroethylene is not removed under the usual conditions which are suitable for removing amylenes. It passes through the sulfuric acid scrubbing with little change and then may be removed by passing the chloroform over a suitable amount of an adsorbent. As will be seen in the examples below, the most effective adsorbents have been found to be 5A zeolites and chabazite. Of these, chabazite, a natural zeolite having the nominal formula $Ca_2Al_4Si_8O_{24}$ has been found to provide the best overall performance. It should be understood that since chabazite is a naturally derived material, it may contain minor amounts of impurities and related minerals with which it is found in nature.

The amount of the adsorbent will depend upon many factors, including the desired degree of removal of cis-1,2-dichloroethylene and the on-stream time before regeneration is needed. Typically a liquid hourly space velocity up to about 9 hr.$^{-1}$ is useful and about 0.08 to 3.5 hr.$^{-1}$ would be preferred. The space velocity chosen will depend on a number of factors which will be familiar to those skilled in the art. The shape of the adsorbent bed may be affected by the temperature of operation since mass transfer considerations may become important at lower temperatures.

The operating pressure preferably will be one which maintains chloroform in the liquid phase at an operating temperature of about 10° to 150° C.

Removing Bromochloromethane

Bromochloromethane is often present in chloroform as a result of bromine contamination of the chlorine used in its manufacture. Since it is converted to the toxic chlorofluoromethane in the fluorination of chloroform, it should be removed from the chloroform feedstock. It has been found that it can be removed by adsorption in a similar manner to cis 1,2-dichloroethylene. That is, 5A zeolites and chabazite are useful for removing bromochloromethane. Chabazite is preferred. Generally, the conditions suitable for cis 1,2-dichloroethylene removal may be used successfully to remove bromochloromethane.

EXAMPLE 1

Sulfuric Acid Treatment

In a series of tests, 25 ml samples of chloroform were mixed with 2 ml of 95% aqueous sulfuric acid and shaken for various periods of time, extending up to 60 minutes. After phase-separating the chloroform, it was passed over calcium hydroxide to remove any traces of acid. The chloroform was then analyzed by gas chromatography using a 3658 mm by 3.175 mm column filled with Carbowax 400 from Alltech Associates which operates at 75° C. and uses helium as a carrier gas (20 ml/min). This column does not separate cis-1,2-dichloroethylene and bromochloromethane and therefore when values for cis-1,2-dichloroethylene (DCE) are reported it is understood that any bromochloromethane present is included. Table 1 below shows the results of these tests.

TABLE 1

| Contact Time | Concentrations in ppm | | | |
|---|---|---|---|---|
| | Amylene | $CCl_4$ | 1,1-Dichloro-ethane | Cis-1,2-Dichloro-ethylene(DCE) |
| Feed $CHCl_3$ | 39 | 155 | 29 | 290 |
| 10 sec. | 0 | 159 | 29 | 289 |
| 1 min. | 0 | 162 | 28 | 291 |
| 5 min. | 0 | 164 | 29 | 291 |
| 10 min. | 0 | 157 | 28 | 305 |
| 30 min. | 0 | 155 | 28 | 293 |
| 60 min. | 0 | 156 | 29 | 289 |

It will be seen that even a short exposure to aqueous sulfuric acid is sufficient to remove all detectable amylenes. It is of interest that carbon tetra chloride, 1,1-dichloroethane and 1,2-dichloroethylene are essentially unaffected.

EXAMPLE 2

Adsorption

In order to screen potential adsorbents, a series of batch tests were carried out in which a sample of the sorbent was placed in a container and a quantity of chloroform added. The mixtures were shaken for two hours while being held at a constant temperature of 25° C. A sample of the treated chloroform was removed and analyzed by gas chromatography using the column described in Example 1. The impurities were measured by flame ionization. The results of these tests are given in Table 2 below.

TABLE 2

| | Fractional Removal A Zeolites | | | | | |
|---|---|---|---|---|---|---|
| $CHCl_3$/ Sorbent | 3A(1) | | 4A(2) | | 5A(3) | |
| g/g | DCE(6) | Amylene | DCE | Amylene | DCE | Amylene |
| 11 | <0.1 | <0.1 | 0.48 | 0.07 | 1.0 | 1.0 |
| 21 | " | " | 0.34 | 0.01 | N/A | N/A |
| 37 | " | " | 0.25 | <0.01 | 0.8 | 0.58 |
| 73 | " | " | 0.2 | " | 0.35 | 0.58 |

| Other Zeolites | | | | | |
|---|---|---|---|---|---|
| AW-300(4) | | | AW-500(5) | | |
| $CHCl_3$/ Sorbent | DCE | Amylene | $CHCl_3$/ Sorbent | DCE | Amylene |
| 11 | 0.1 | 0.25 | 11 | 1.0 | 1.0 |
| 21 | 0.05 | 0.15 | 27 | 0.95 | " |
| 42 | 0.04 | 0.12 | 35 | 0.60 | " |
| 67 | 0.04 | 0.09 | 72 | 0.1 | " |

(1)Aldrich Chemical Co.
(a)VOP Inc.
(3)VOP Inc.
(4)Mordenite - UOP
(5)Chabazite - UOP
(6)cis-1,2,dichloroethylene (+ bromochloromethane)

It can be seen that selection of a suitable adsorbent requires experimentation since a potential adsorbent may show no capacity for the components (e.g. 3A zeolite), capacity for both (e.g. 5A zeolite, AW-500), or capacity for one component and not the other (e.g. 4A zeolite). Based on the data of Table 2, 5A zeolites or AW-500 (a calcium chabazite) would appear promising as potential absorbents. Indeed, they have a similar pore size and superficially might be considered comparable. However, it has been found that 5A zeolites are not satisfactorily regenerated, contrary to the report in published Japanese application 62207/77, and consequently, chabazite is preferred.

Although not shown in Table 2, other zeolites were tested with generally poor results, if the criteria is to obtain a substantial recovery of both amylenes and 1,2-dichloroethylene. Examples of such materials are cation exchanged X zeolites (crystallographic pore size 7.3 Å), Y zeolites (crystallographic pore size 7.4 Å), and silicalite (crystallographic pore size 5.4×5.6 Å).

EXAMPLE 3

(comparative)

A series of tests were carried out following the procedures of Example 2 with zeolites and other adsorbents which were found to have little value in removing the impurities, as will be seen in the results tabulated below.

TABLE 3

| | Fractional Removal Sorbent | | | | | | | |
|---|---|---|---|---|---|---|---|---|
| $CHCl_3$/ Sorbent. | NaX(a) | | KX(b) | | CaX(c) | | NaY(d) | |
| g/g | DCE | Amylene | DCE | Amylene | DCE | Amylene | DCE | Amylene |
| 5 | 0.11 | N/A | 0.15 | 0.4 | — | — | — | — |
| 11 | <0.05 | N/A | 0.02 | 0.5 | 0.2 | 0.77 | 0.21 | 0 |
| 23 | — | — | 0 | 0.55 | 0.1 | 0.46 | 0.12 | <0.01 |

| $CHCl_3$/ Sorbent | CaY(e) | | HY(f) | | Silicalite(g) | | LaPorte#7(h) | |
|---|---|---|---|---|---|---|---|---|
| g/g | DCE | Amylene | DCE | Amylene | DCE | Amylene | DCE | Amylene |
| 11 | 0.21 | 1.0 | 0.26 | 1.0 | 0.05 | 0.05 | 0.11 | 0.97 |
| 23 | 0.11 | 0.95 | 0.14 | 1.0 | 0.04 | 0.04 | 0.07 | 0.95 |

| $CHCl_3$/ Sorbent | Florisil(i) | | BPKaldair(j) | |
|---|---|---|---|---|
| g/g | DCE | Amylene | DCE | Amylene |
| 11 | 0 | <0.05 | 0.02 | 0.045 |
| 23 | 0 | <0.05 | 0.01 | 0.018 |

(a)VOP
(b)by ion exchange of NaX(a)
(c)VOP UOP
(d)VOP
(e)VOP
(f)VOP
(g)VOP
(h)La Porte Industries
(i)Floriden Inc.
(j)BP Kaldair It has been found that, although Japanese published application 62207/77 suggests that regeneration at 300° C. is suitable, that regeneration at any temperature of 5A zeolites is unsatisfactory in this service, as will be seen in the experiments described below. The Japanese application shows that capacity for cis-1,2,-dichloroethylene is reduced after regeneration. Indeed, regeneration at 300° C. would be expected to cause a loss of surface area. The present inventors found that regeneration at lower temperatures did not occur, while chabazite could be regenerated.

EXAMPLE 4

Ten(10) grams of a zeolite were placed in a 10 mm diameter column and chloroform was passed over the zeolite at a flow rate of 5 ml/min. After breakthrough of the DCE had occurred as measured by the procedures of Example 1, the zeolite was transferred to furnace where it was heated to the temperature indicated in Table 4 while being subjected to a vacuum of 1 torr. Such tests were carried out using 5A zeolite and AW-500, a calcium chabazite. The results of the tests are given in Table 4 below.

TABLE 4

| Amt. of $CHCl_3$ passed over absorbent (g/g) | Outlet Concentration of DCE/wgt. ppm | | | | | |
|---|---|---|---|---|---|---|
| | 5A Zeolite | | | AW-500 | | |
| | Fresh | Regen. @100° C. | Regen. @200° C. | Fresh | Regen. @100° C. | Regen. @300° C. |
| 20 | 30 | 260 | 240 | 35 | 95 | 30 |
| 40 | 60 | 270 | 245 | 60 | 145 | 55 |
| 60 | 110 | n/a | 250 | 90 | 185 | 95 |
| 80 | 210 | n/a | 255 | 115 | 225 | 115 |
| 100 | n/a | n/a | n/a | n/a | 245 | 140 |

It was concluded that AW-500 provided clearly superior performance since it could be regenerated at reasonable temperatures, while 5A zeolite could not.

EXAMPLE 5

High Temperature Adsorption

In an experiment similar to that of Example 4, 10 gm of AW-500 chabazite was placed in a 6 mm diameter column and maintained at a temperature of 150° C. Impure chloroform containing about 700 wt. ppm of DCE was passed over the zeolite and the product was analyzed by the procedures of Example I. The results shown below indicate that impurities can be removed at temperatures well above ambient, however, the capacity of the zeolite was reduced. The analysis suggests that at these temperatures some decomposition of the chloroform may have occurred.

| Amt of $CHCl_3$ passed over adsorbent, g/g | Outlet Concentration of DCE (wt.-ppm.) |
|---|---|
| 12.68 | <1.0 |
| 25.36 | <1.0 |
| 38.05 | 40 |
| 50.73 | 468 |
| 63.41 | 677 |
| 76.09 | 711 |
| 88.77 | 652 |

Two-step Process for Chloroform Purification

Purification of chloroform requires at least removal of cis-1,2-dichloroethylene, bromochloromethane, and amylenes when the chloroform is to be used as a feedstock for chlorodifluoromethane (R-22) production as has been discussed above. These impurities may be up to about 1000 wt ppm each, but typically they will be present in amounts between about 50-500 wt. ppm. Preferably, the process will be carried out in two steps to most effectively apply the methods of the invention. In the first step, chloroform will be contacted with aqueous sulfuric acid to remove amylenes. A 80 to 100 wt.% solution will be suitable, and 90 to 96 wt.% is preferred. Contacting will take place in a batch or continuous manner using various techniques known to the art.

In a batch process the volume ratio of acid to chloroform may be from about 1:50 to 1:800. Generally, continuous contacting in a liquid-liquid extractor with would be preferred to provide complete removal of amylenes while continuously feeding the fluorination process. In a continuous process the volume ratio of acid to chloroform will generally be up to about 1:10 to assure good contacting. Since only a little acid reacts, it would usually be recirculated to maintain the desired ratio. A contact time of 5 sec to 10 min, preferably 10 sec to 30 sec. will be suitable. The temperature may be 10° to 150° C., typically 20° to 80° C. As shown in Example 1 above, such contacting can remove substantially all of the amylenes while leaving untouched other impurities.

The amylene-free chloroform will thereafter be passed over an effective amount of an adsorbent to remove both cis-1,2-dichloroethylene and bromochloromethane. The preferred adsorbent is chabazite since it can be repeatedly regenerated. A liquid hourly space velocity of up to about 9 $hr^{-1}$ will be suitable, but about 0.08 to 3.5 $hr^{-1}$ is preferred. The operating temperature may be 10° to 200° C. with 20° to 80° C. being preferred. In general, a fixed bed contactor would be used, although other liquid-solids contactors may be used, such as mixer-settlers. As will have been seen in Example 2 above, chabazite will remove a large fraction of the cis-1,2-dichloroethylene and bromochloromethane, typically up to 95% or more.

Regeneration

The adsorbent will require regeneration in many instances and it has been found that chabazite is regenerable while 5A zeolites lose surface area and effectiveness when regenerated, as will be seen in Example 4 above. The most effective methods of regenerating chabazite will be discussed below; in general, it has been found that chabazite can be regenerated fully and returned to near-fresh condition by employing a multistep procedure intended to be integrated with the fluorination of chloroform to CHClF2.

When the impurities begin to break through the adsorbent bed after a period of use, it is necessary to regenerate the bed, usually while continuing to remove impurities with a second already-regenerated bed. The saturated bed will be first freed of residual chloroform by purging with a stream of an inert gas, such as nitrogen, carbon dioxide, argon or helium. This chloroform-laden gas may be separated by condensation and the chloroform returned to the feed to the on-stream adsorbent bed. It would be undesirable to return the chloroform if it contains a large amount of the impurities, consequently the purging step should be carried out under conditions selected to avoid substantial desorption of the impurities. In a preferred embodiment of the invention, nitrogen gas is passed at a gas hourly space velocity of about 2000 hr$^{-1}$ over bed while maintaining a temperature of about 25° C. and a pressure of about 100 kPa for a sufficient period of time to purge substantially all of the chloroform from the adsorbent bed.

After purging the bed regeneration may proceed, which requires elevated temperatures and preferably subatmospheric pressures. An inert gas is introduced at a temperature in the range of about 100° to 200° C. and removed from the outlet end of the bed and passed through a separation step to remove chloroform containing a large concentration of the impurities. The gas will be passed over the bed at a gas hourly space velocity of about 40-50 hr$^{-1}$ while maintaining a pressure of about 7 kPa until substantially all of the impurities have been removed. This may require from 1 to 7 hrs. Following the regeneration, the gas is passed over the bed at about ambient temperature to cool and prepare it for further service.

What is claimed:

1. A process for removing impurities from chloroform comprising up to about 1000 wt ppm each of cis-1,2-dichloroethylene, bromochloromethane, and amylenes comprising:

(a) contacting said chloroform with an 80 to 100 wt.% aqueous solution of sulfuric acid to remove substantially all of the amylenes therefrom and phase separating said chloroform; and, (b) passing the chloroform after the separation of (a) over an effective amount of a zeolite having an average pore diameter between about 3 to 6 Angstroms and a Si/Al atomic ratio of about 1.6/1 to 3/1 to remove substantially all of said cis-1,2-dichloroethylene and bromochloromethane.

2. The process of claim 1 wherein the chloroform after step (b) contains less than 100 wt. ppm of cis-1,2-dichloroethylene, bromochloromethane, and amylenes.

3. The process of claim 1 wherein said zeolite is calcium chabazite.

4. The process of claim 1 wherein said aqueous solution contains at least about 90 wt.% sulfuric acid.

5. The process of claim 1 wherein chloroform is contacted with aqueous sulfuric acid in step (a) for at least 5 seconds.

6. The process of claim 1 wherein the volume ratio of acid to chloroform is 1:50 to 1:800.

7. The process of claim 1 wherein chloroform is contacted with aqueous sulfuric acid in step (a) at a temperature of about 10° to 150° C.

8. The process of claim 1 wherein step (b) is carried out at a liquid hourly space velocity of up to 9 hr$^{-1}$.

9. The process of claim 1 wherein step (b) is carried out at a temperature of about 10° to 150° C.

* * * * *